US012137977B2

United States Patent
Rafaeli et al.

(10) Patent No.: US 12,137,977 B2
(45) Date of Patent: *Nov. 12, 2024

(54) RETINAL IMAGING DEVICE AND RELATED METHODS

(71) Applicant: Notal Vision Ltd., Tel Aviv (IL)

(72) Inventors: Omer Rafaeli, Udim (IL); Muki Rapp, Ramat Gan (IL); Hanoch Gideon Benyamini, Ramat Hasharon (IL); Yair Alster, Tel Aviv (IL); Eitan Sharif, Kibbutz Gesher Haziv (IL); Amit Pascal, Haifa (IL)

(73) Assignee: Notal Vision, Ltd., Tel Aviv (IL)

( * ) Notice: Subject to any disclaimer, the term of this patent is extended or adjusted under 35 U.S.C. 154(b) by 749 days.

This patent is subject to a terminal disclaimer.

(21) Appl. No.: 17/345,228

(22) Filed: Jun. 11, 2021

(65) Prior Publication Data

US 2021/0369110 A1 Dec. 2, 2021

Related U.S. Application Data

(63) Continuation of application No. 16/404,311, filed on May 6, 2019, now Pat. No. 11,058,299, which is a
(Continued)

(51) Int. Cl.
*A61B 3/12* (2006.01)
*A61B 3/00* (2006.01)
(Continued)

(52) U.S. Cl.
CPC ............ *A61B 3/12* (2013.01); *A61B 3/102* (2013.01); *A61B 3/14* (2013.01); *A61B 3/15* (2013.01); *A61B 3/152* (2013.01); *A61B 3/0008* (2013.01);

(58) Field of Classification Search
CPC ............ A61B 3/132; A61B 3/12; A61B 3/102; A61B 3/14; A61B 3/15; A61B 3/152; A61B 3/18
See application file for complete search history.

(56) References Cited

U.S. PATENT DOCUMENTS

| 4,786,142 A | 11/1988 | Karecki | |
| 5,094,521 A * | 3/1992 | Jolson | A61B 3/11 |
| | | | 351/210 |

(Continued)

FOREIGN PATENT DOCUMENTS

| CN | 102551654 A | 7/2012 |
| CN | 103957774 A | 7/2014 |

(Continued)

OTHER PUBLICATIONS

Chakravarthy et al., "Automated Identification of Lesion Activity in Neovascular Age-Related Macular Degeneration", Opthalmology, vol. 123, No. 8, Aug. 2016, 6 pages.
(Continued)

*Primary Examiner* — Ephrem Z Mebrahtu
(74) *Attorney, Agent, or Firm* — Kilpatrick Townsend & Stockton LLP

(57) ABSTRACT

Ophthalmic imaging devices and related methods employ self-alignment of a user with an optical axis of the imaging device. An ophthalmic imaging device includes a retinal imaging assembly, a housing assembly, and a viewer assembly. The retinal imaging assembly has an optical axis. The retinal imaging assembly is attached to the housing. The housing assembly is configured to rest on a horizontal surface during operation of the retinal imaging assembly. The optical axis is oriented at an angle from the horizontal surface when the housing assembly rests on the horizontal surface. The viewer assembly is coupled with the housing assembly. The viewer assembly includes an interface surface
(Continued)

shaped for engagement with each head of a plurality of different user's and to accommodate repositioning of the head to align a pupil of the user with the optical axis.

17 Claims, 7 Drawing Sheets

Related U.S. Application Data continuation-in-part of application No. PCT/IL2018/051174, filed on Nov. 4, 2018.

(60) Provisional application No. 62/582,772, filed on Nov. 7, 2017.

(51) Int. Cl.
  *A61B 3/10* (2006.01)
  *A61B 3/14* (2006.01)
  *A61B 3/15* (2006.01)

(56) References Cited

U.S. PATENT DOCUMENTS

| | | | |
|---|---|---|---|
| D390,662 S | 2/1998 | Cooper | |
| 5,838,424 A * | 11/1998 | Wawro | A61B 3/02 351/200 |
| 6,149,275 A | 11/2000 | O'Shea | |
| 6,980,363 B1 | 12/2005 | Takagi et al. | |
| 7,270,413 B2 | 9/2007 | Hirohara et al. | |
| D614,774 S | 4/2010 | Gausmann et al. | |
| 7,942,527 B2 | 5/2011 | Olivier et al. | |
| 8,064,989 B2 | 11/2011 | Brown et al. | |
| 8,098,278 B2 | 1/2012 | Yumikake et al. | |
| 8,123,354 B2 | 2/2012 | Olivier et al. | |
| 8,348,429 B2 | 1/2013 | Walsh et al. | |
| 8,374,684 B2 | 2/2013 | Buckland et al. | |
| 8,384,908 B2 | 2/2013 | Sugita et al. | |
| 8,398,236 B2 | 3/2013 | Juhasz et al. | |
| 8,421,855 B2 | 4/2013 | Buckland et al. | |
| 8,459,794 B2 | 6/2013 | Juhasz et al. | |
| 8,500,725 B2 | 8/2013 | Raksi | |
| 8,534,835 B2 | 9/2013 | Murata et al. | |
| 8,534,837 B2 | 9/2013 | Sayeram et al. | |
| 8,668,336 B2 | 3/2014 | Buckland et al. | |
| D705,430 S | 5/2014 | Sekine | |
| 8,804,127 B2 | 8/2014 | Shimoyama et al. | |
| 8,820,931 B2 | 9/2014 | Walsh et al. | |
| 8,842,287 B2 | 9/2014 | Yazdanfar et al. | |
| 8,860,796 B2 | 10/2014 | Buckland et al. | |
| 8,960,903 B2 | 2/2015 | Horn et al. | |
| 8,960,905 B2 | 2/2015 | Aoki et al. | |
| 9,044,166 B2 | 6/2015 | Murata et al. | |
| 9,144,379 B1 * | 9/2015 | Sims | A61B 3/12 |
| 9,149,182 B2 | 10/2015 | Walsh et al. | |
| 9,170,087 B2 | 10/2015 | Makihira et al. | |
| 9,173,563 B2 | 11/2015 | Buckland et al. | |
| 9,186,057 B2 | 11/2015 | Borycki et al. | |
| 9,192,295 B1 | 11/2015 | Hathaway et al. | |
| 9,273,950 B2 | 3/2016 | Yazdanfar et al. | |
| 9,277,859 B2 | 3/2016 | Oyaizu et al. | |
| 9,277,860 B2 | 3/2016 | Komine et al. | |
| 9,314,154 B2 | 4/2016 | Palanker et al. | |
| 9,420,947 B2 | 8/2016 | Wei et al. | |
| 9,427,151 B2 | 8/2016 | Horn et al. | |
| 9,492,079 B2 | 11/2016 | Walsh et al. | |
| 9,538,916 B2 | 1/2017 | Muto | |
| 9,565,999 B2 | 2/2017 | Takai | |
| 9,572,484 B2 | 2/2017 | Palanker et al. | |
| 9,622,658 B2 | 4/2017 | Hart et al. | |
| 9,814,383 B2 | 11/2017 | Hart et al. | |
| D808,527 S | 1/2018 | Wing et al. | |
| 9,888,841 B2 | 2/2018 | Hogan | |
| D812,759 S | 3/2018 | Sekine et al. | |
| 9,907,466 B2 | 3/2018 | Kowal et al. | |
| 10,048,055 B2 | 8/2018 | Lim et al. | |
| 10,092,180 B2 | 10/2018 | Hart et al. | |
| 10,165,941 B2 | 1/2019 | Walsh et al. | |
| D847,345 S | 4/2019 | Iliffe-moon et al. | |
| 10,251,549 B2 | 4/2019 | Sarunic et al. | |
| 10,314,480 B2 | 6/2019 | Ishiai | |
| 10,327,632 B2 | 6/2019 | Horn | |
| 10,595,722 B1 | 3/2020 | Pascal et al. | |
| 10,610,096 B2 | 4/2020 | Scheibler et al. | |
| 10,653,309 B2 | 5/2020 | Shimozato et al. | |
| 10,653,311 B1 | 5/2020 | Pascal et al. | |
| 10,653,314 B2 | 5/2020 | Pascal et al. | |
| 2003/0063386 A1 * | 4/2003 | Slawson | A61B 3/12 359/600 |
| 2003/0086059 A1 | 5/2003 | Percival et al. | |
| 2005/0024586 A1 | 2/2005 | Teiwes et al. | |
| 2008/0259274 A1 | 10/2008 | Chinnock | |
| 2009/0180074 A1 | 7/2009 | Benyamini et al. | |
| 2009/0268020 A1 | 10/2009 | Buckland et al. | |
| 2013/0033593 A1 | 2/2013 | Chinnock et al. | |
| 2013/0162948 A1 | 6/2013 | Yazdanfar et al. | |
| 2013/0208241 A1 | 8/2013 | Lawson et al. | |
| 2013/0235344 A1 | 9/2013 | Buckland et al. | |
| 2014/0002792 A1 | 1/2014 | Filar | |
| 2014/0009741 A1 | 1/2014 | Levien et al. | |
| 2014/0046193 A1 * | 2/2014 | Stack | A61B 3/113 600/476 |
| 2014/0125952 A1 | 5/2014 | Buckland et al. | |
| 2014/0132924 A1 | 5/2014 | Sagano et al. | |
| 2014/0240674 A1 | 8/2014 | Wei et al. | |
| 2014/0340642 A1 | 11/2014 | You et al. | |
| 2015/0042951 A1 | 2/2015 | Stanga et al. | |
| 2015/0208913 A1 | 7/2015 | Watanabe et al. | |
| 2015/0292860 A1 | 10/2015 | Podoleanu et al. | |
| 2015/0294147 A1 | 10/2015 | Wisweh | |
| 2015/0305618 A1 | 10/2015 | Buckland et al. | |
| 2015/0313467 A1 | 11/2015 | Sakai et al. | |
| 2016/0026847 A1 | 1/2016 | Vugdelija et al. | |
| 2016/0135681 A1 | 5/2016 | Wakil et al. | |
| 2016/0143529 A1 | 5/2016 | Miyashita et al. | |
| 2016/0183788 A1 | 6/2016 | Abramoff et al. | |
| 2016/0302665 A1 | 10/2016 | Swedish et al. | |
| 2017/0042422 A1 | 2/2017 | Sakai et al. | |
| 2017/0049318 A1 | 2/2017 | Walsh et al. | |
| 2017/0071466 A1 | 3/2017 | Kowal et al. | |
| 2017/0143202 A1 | 5/2017 | Palanker et al. | |
| 2017/0172407 A1 * | 6/2017 | Kowal | A61B 3/1225 |
| 2017/0215725 A1 | 8/2017 | Ishiai | |
| 2017/0224208 A1 | 8/2017 | Bublitz et al. | |
| 2017/0227350 A1 | 8/2017 | Sarunic et al. | |
| 2017/0251920 A1 | 9/2017 | Tokuda et al. | |
| 2018/0296087 A1 | 10/2018 | Carrasco-Zevallos et al. | |
| 2019/0090733 A1 | 3/2019 | Walsh et al. | |
| 2019/0090735 A1 | 3/2019 | Fujii et al. | |
| 2019/0254514 A1 * | 8/2019 | Westphal | A61B 3/102 |
| 2019/0254518 A1 | 8/2019 | Rafaeli et al. | |
| 2019/0313895 A1 | 10/2019 | Hayashi et al. | |
| 2019/0368861 A1 | 12/2019 | Wax et al. | |

FOREIGN PATENT DOCUMENTS

| | | |
|---|---|---|
| JP | 2011251061 A | 12/2011 |
| JP | 2014073248 A | 4/2014 |
| JP | 2017148241 A | 8/2017 |
| WO | 2012149056 A1 | 11/2012 |
| WO | 2016004385 A1 | 1/2016 |
| WO | 2017190087 A1 | 11/2017 |
| WO | 2019147871 A1 | 8/2019 |
| WO | 2019246412 A1 | 12/2019 |
| WO | 2020056454 A1 | 3/2020 |

OTHER PUBLICATIONS

Application No. EP18876516.8, Extended European Search Report Mailed on Jun. 1, 2021, 10 pages.
Application No. PCT/IL2018/051172, International Search Report and Written Opinion Mailed on Feb. 27, 2019, 12 pages.

(56) References Cited

OTHER PUBLICATIONS

Application No. PCT/IL2018/051174, International Search Report and Written Opinion Mailed on Feb. 26, 2019, 8 pages.

* cited by examiner

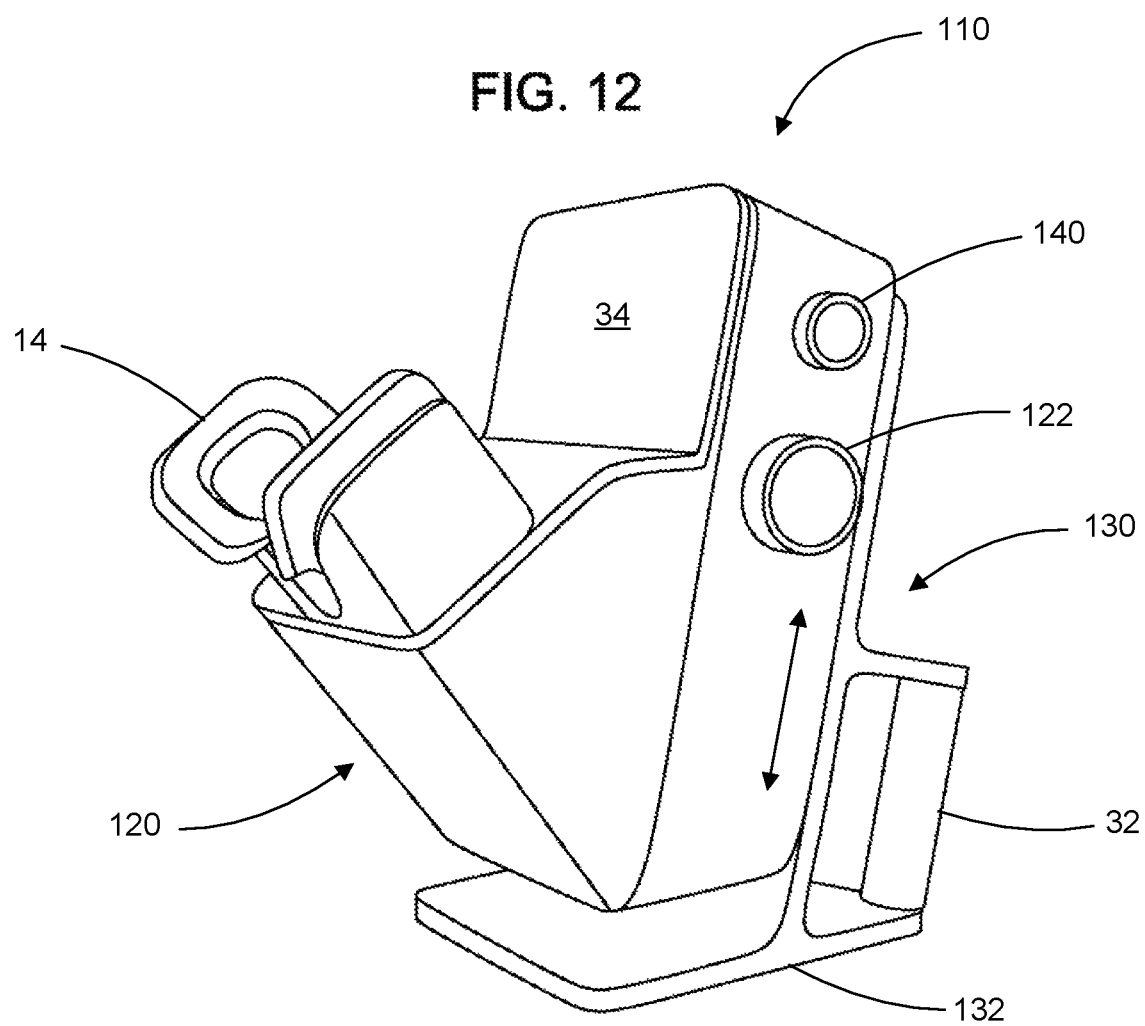

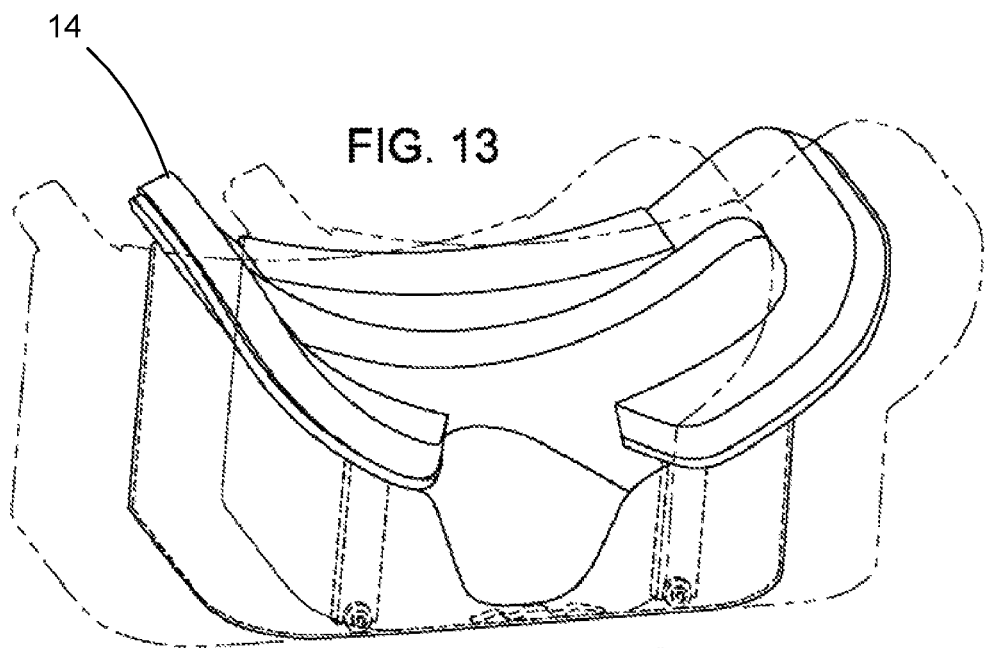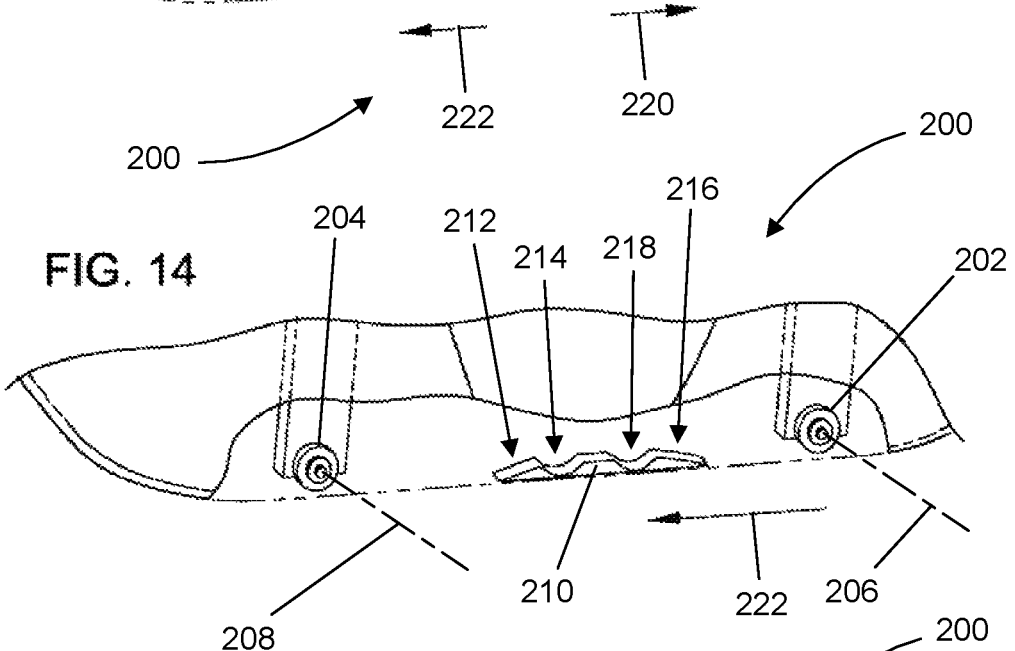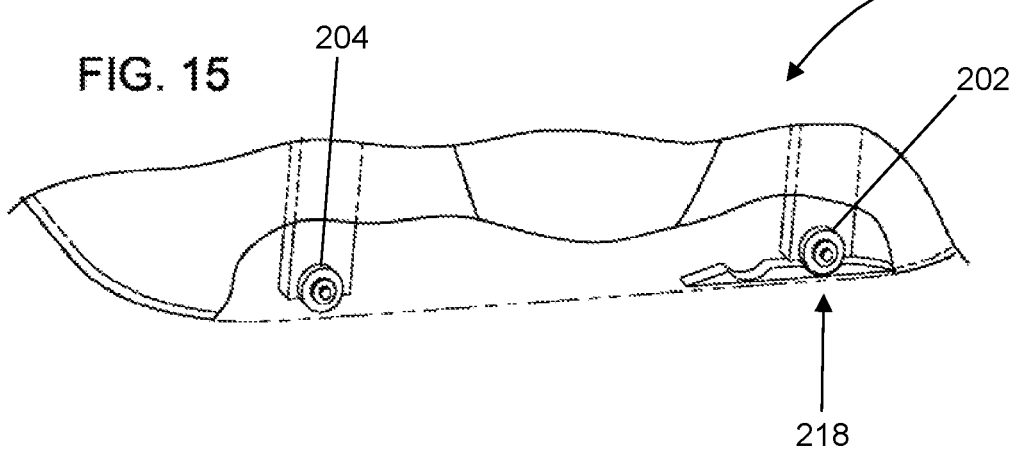

RETINAL IMAGING DEVICE AND RELATED METHODS

CROSS REFERENCE TO RELATED APPLICATIONS

The present application is a Continuation of U.S. patent application Ser. No. 16/404,311, filed May 6, 2019, which is a Continuation-in-Part of International Application No. PCT/IL2018/051174, filed Nov. 4, 2018, which claims the benefit of U.S. Provisional Application Ser. No. 62/582,772, filed on Nov. 7, 2017, all of which are incorporated by reference herein in their entirety for all purposes.

BACKGROUND

Macular degeneration is the leading cause of vision loss in the United States of America. In macular degeneration, the central portion of the retina (a.k.a., the macula) deteriorates. When healthy, the macula collects and sends highly detailed images to the brain via the optic nerve. In early stages, macular degeneration typically does not significantly affect vision. If macular degeneration progresses beyond the early stages, vision becomes wavy and/or blurred. If macular degeneration continues to progress to advanced stages, central vision may be lost.

Although macular degeneration is currently considered to be incurable, treatments do exist that may slow the progression of the disease so as to prevent severe loss of vision. Treatment options include injection of an anti-angiogenic drug into the eye, laser therapy to destroy an actively growing abnormal blood vessel(s), and photodynamic laser therapy, which employs a light-sensitive drug to damage an abnormal blood vessel(s). Early detection of macular degeneration is of paramount importance in preventing advanced progression of macular degeneration prior to treatment to inhibit progression of the disease. Timely treatment of advanced AMD is important to maintain the patient's vision.

Early detection of macular degeneration and timely treatment decisions can be accomplished using a suitable retinal imaging system. For example, Optical Coherence Tomography (OCT) is a non-invasive imaging technique relying on low coherence interferometry that can be used to generate a cross-sectional image of the macula. The cross-sectional view of the macula shows if the layers of the macula are distorted and can be used to monitor whether distortion of the layers of the macula has increased or decreased relative to an earlier cross-sectional image to assess the impact of treatment of the macular degeneration.

Existing OCT imaging systems, however, are typically expensive and may have to be operated by a trained technician. For example, a trained technician may be required to properly align an optical axis of the OCT imaging system with the optical axis of the eye examined. As a result, the use of such OCT imaging systems is typically restricted to specialized eye care clinics, thereby limiting use of such OCT imaging systems for widespread screening for early stage macular degeneration. Alternatively, the alignment can be performed automatically by a closed loop control system utilizing imaging, processing, and motors to achieve the required positioning. Another example would be fundus camera that requires a technician or a motorized control loop to align the optical axis with the patient pupil to be able to take an image of the retina.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

Ophthalmic imaging devices and related methods orient an optical axis of the imaging device at an angle from 45 degrees to 85 degrees from a horizontal surface on which the ophthalmic imaging device is supported and employ a viewer assembly that stabilizes the user's head in a suitable position and orientation relative to the optical axis. In many embodiments, the imaging device conducts imaging over a relatively long period of time (e.g., 30 seconds) and the user engages the user's head with the viewer assembly to stabilize the position and orientation of the user's head relative to the optical axis over the imaging period. In many embodiments, the viewer assembly accommodates different positions and/or orientations of the user's head relative to the optical axis so as to enable alignment, by the user, of one of the user's eyes with the optical axis. The combination of the optical axis being angled relative to horizontal and the configuration of the viewer assembly enables the user to self-align an eye of the user with the optical axis and maintain the position of the eye relative to the optical axis over the imaging period while sitting in a natural, comfortable position. Moreover, the combination of the optical axis being angled relative to horizontal and the configuration of the viewer assembly effectively inhibits gravity induced downward drift movement by the user during the imaging period.

Thus, in many embodiments, an ophthalmic imaging device includes an imaging assembly having an optical axis, a housing assembly to which the imaging assembly is attached, and a viewer assembly coupled with the housing assembly. The housing assembly is configured to rest on a horizontal surface during operation of the imaging assembly. The optical axis is oriented at an angle from 45 degrees to 85 degrees from the horizontal surface when the housing assembly rests on the horizontal surface. The viewer assembly includes an interface surface shaped to engage a user's head to stabilize a position and an orientation of the user's head relative to the optical axis. The viewer assembly accommodates different positions and/or orientations of the user's head relative to the optical axis so as to enable alignment, by the user, of one of the user's eyes with the optical axis.

In many embodiments, the viewer assembly is adapted to block light when engaged by a user's head to create a dark environment to dilate the user's pupil to enhance imaging of the user's retina. For example, in some embodiments, the interface surface is configured to engage the user's head continuously along a perimeter segment that surrounds the user's eyes. In such embodiments, the perimeter segment can extend continuously from below the user's left eye, around the user's left eye between the user's left eye and the user's left ear, above the user's eyes, around the user's right eye between the user's right eye and the user's right ear, to below the user's right eye.

In many embodiments, the interface surface is configured to accommodate the different positions and/or orientations of the user's head relative to the optical axis. For example, the interface surface can be sized and/or shaped to accommodate the different positions and/or orientations of the user's head relative to the optical axis.

In many embodiments, the ophthalmic imaging device includes an aperture through which the imaging assembly images the one of the user's eyes aligned with the optical axis. In many embodiments, the viewer assembly comprises a light blocking side surface that extends between the interface surface and the aperture to block light continuously along the interface surface.

In many embodiments, the viewer assembly is deformable so that the shape of interface surface is conformable to the user's head to accommodate the different positions and/or orientations of the user's head relative to the optical axis. For example, in some embodiments, the viewer assembly includes a base component, a deformable component mounted to the base component, and a biocompatible layer that covers the deformable component. In such embodiments, the biocompatible layer can include the interface surface.

In many embodiments, the viewer assembly can be used any of many different users. For example, in many embodiments the viewer assembly accommodates different positions and/or orientations of each of a plurality of different user's heads relative to the optical axis so as to enable alignment, by the respective user, of one of the respective user's eye with the optical axis. In such embodiments, the plurality of different users includes a plurality of different distances by which the eyes of the respective user are separated.

In many embodiments, the viewer assembly is configured to engage with stable portions of the user's head. For example, in many embodiments, the interface surface is configured to engage the user's forehead and/or the user's cheeks.

In many embodiments, the imaging assembly has a focal point. In many embodiments, the focal point is disposed at a height between 180 mm to 350 mm above the horizontal surface when the housing assembly rests on the horizontal surface. In many embodiments, the housing assembly is adjustable to change the height at which the focal point is disposed above the horizontal surface. For example, the housing assembly can include a pair of legs that can be adjusted to change the height at which the focal point is disposed above the horizontal surface. In some embodiments, the housing assembly is adjustable to simultaneously change the height at which the focal point is disposed above the horizontal surface and the orientation of the optical axis relative to the horizontal surface. In such embodiments, each respective height can have a corresponding unique angle of the optical axis relative to the horizontal surface.

In many embodiments, the viewer assembly is adapted to enable a suitable range of positions and/or orientations of the user's head relative to the optical axis. For example, in many embodiments, the different positions and/or orientations of the user's head accommodated by the viewer assembly enable repositioning of the user's eye by 20 mm along any axis perpendicular to the optical axis.

In many embodiments, the ophthalmic imaging device is adapted to be restrained by the user to hold the viewer assembly in engagement with the user's head. For example, the housing assembly can include a pair of handles configured to be held by the user to hold the viewer assembly in engagement with the user's head.

In many embodiments, the ophthalmic imaging device is reconfigurable between a configuration for imaging the user's right eye retina and a configuration for imaging the user's left eye retina. For example, in many embodiments, the ophthalmic imaging device includes a repositioning mechanism by which the viewer assembly is coupled to the housing assembly. In such embodiments, the repositioning mechanism can be configured to enable repositioning of the viewer assembly relative to the housing assembly to enable separate alignment of each of the user's eyes with the optical axis. In some embodiments, the viewer assembly is slideably coupled with the housing assembly via the repositioning mechanism. In some embodiments, the viewer assembly is slideably relative to the housing assembly via the repositioning mechanism in two different directions transverse to the optical axis. In some embodiments, the repositioning mechanism is operable to reposition the viewer assembly relative to the focal point parallel to the optical axis.

In some embodiments, the housing assembly is adjustable to change the angle at which the optical axis is oriented relative to the horizontal surface. For example, in some embodiments, the housing assembly includes a pair of legs that can be adjusted to change the angle at which the optical axis is oriented relative to the horizontal surface.

For a fuller understanding of the nature and advantages of the present invention, reference should be made to the ensuing detailed description and accompanying drawings.

BRIEF DESCRIPTION OF THE DRAWINGS

FIG. 12 shows an isometric view image of another ophthalmic imaging device, in accordance with many embodiments.

FIG. 13, FIG. 14, and FIG. 15 illustrate a locking mechanism that inhibits sliding of the viewer assembly relative to the housing assembly while the viewer assembly is engaged by the user's head, in accordance with many embodiments.

DETAILED DESCRIPTION

Figure 1:
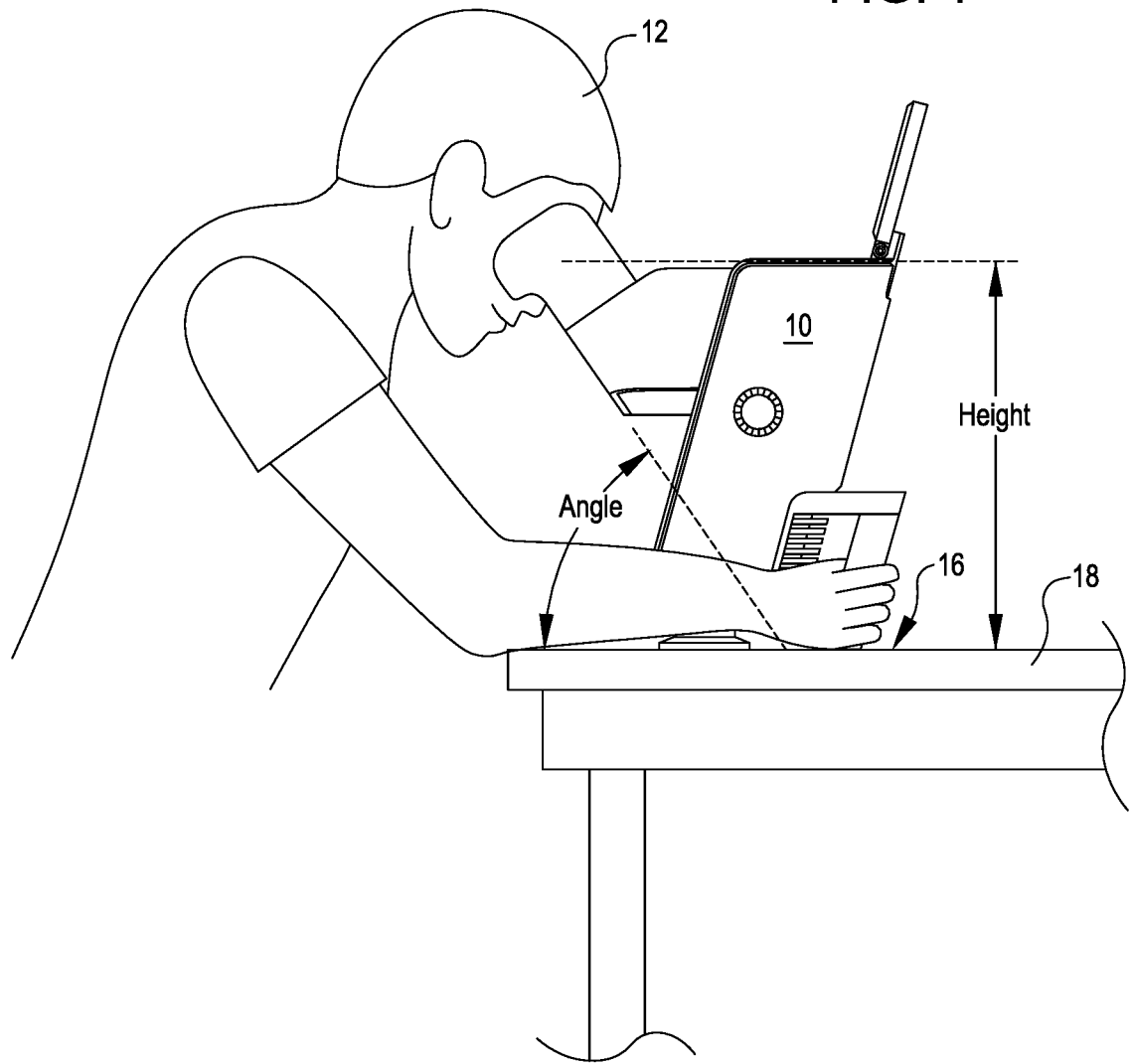
FIG. 1 is a side view illustrating a user engaged with an ophthalmic imaging device via a viewer assembly that accommodates self-alignment of the user with an optical axis of the ophthalmic imaging device, in accordance with many embodiments.

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Introduction

Many patients with retinal diseases are treated with intra-ocular injection per general guidelines based on the average patient. Progression of a retinal disease in any specific patient, may progress differently than in the average patient. Moreover, the specific patient may respond differently to treatment than the average patient. Accordingly, there is a strong clinical need to monitor the progression of a retinal disease in some patients on a continual basis so that the patient can receive treatment based on their own disease progression. Ophthalmic imaging devices employing optical coherence tomography (OCT) imaging are often employed in eye clinics image a patient's retina to monitor the progression of a retinal disease. Having to travel to an eye clinic, however, may prevent sufficient continual monitoring in some patients. As a result, there is a need for affordable OCT based ophthalmic imaging devices that can be used by a patient at home to continually monitor the progression of the patient's retinal disease. Such retinal disease may be chorio-retinal eye diseases, such as AMD, ocular hystoplasmosis, myopia, central serous retinopathy, central serous choroidopathy, glaucoma, diabetic retinopathy, retintis pigmentosa, optic neuritis, epiretinal membrane, vascular abnormalities and/or occlusions, choroidal dystrophies, retinal dystrophies, macular hole, or choroidal or retinal degeneration.

In many embodiments, an affordable ophthalmic retinal imaging device (e.g., an affordable ophthalmic retinal imaging device that employs OCT imaging, an affordable ophthalmic retinal imaging device that employs a fundus camera and an additional retinal imaging device) presents a few challenges relative to alignment of a patient's eye with an optical axis of the imaging device. For example, the patient's pupil needs to be centered (e.g., in two directions transvers to the optical axis) and stable relative to the optical axis of the imaging device throughout the imaging time period. The patient needs to be fixated (e.g., gazing at a fixation target) throughout the imaging time period. The patient's retina needs to be at a suitable location along the optical axis throughout the imaging time period. Many patients, however, especially elderly patients, find it very hard to maintain suitable position and orientation of their eye relative to the imaging device through the applicable imaging time period.

As a result, ophthalmic retinal imaging devices that are employed at an eye clinic typically require significant technician assistance, include pricy hardware, and/or employ sophisticated algorithms to compensate for a patient's inability to maintain suitable position and orientation of their eye relative to the imaging device through the applicable imaging time period. For example, a clinic may often employ a technician who watches a monitor in real time to monitor positions of the patient's pupil and retina, operate an alignment device to align the imaging device with the patient's eye, and/or provide instruction to the patient on what to do to align and/or maintain alignment of the imaging device with the patient's eye. There are also ophthalmic imaging devices that include an auto-alignment system employing high scanning speed eye tracking to automatically maintain alignment of the imaging device with the patient's eye. Such auto-alignment systems, however, are typically expensive and unsuitable for mass production. There also ophthalmic imaging devices that employ anatomical land mark registration (blood vessels in the case or retinal imaging) to correct for movement and/or changes in orientation of the patient's eye relative to the imaging device during the imaging period. Such anatomical land mark registration, however, typically employs a fundus camera, which again increases the costs of the imaging device and renders the imaging device unsuitable for mass production. Moreover, certain regions of the eye, such as the central portion of the macula, do not have a blood vessel suitable for use as a visible landmark.

Moreover, simply asking a patient to fixate on a target and not move is typically insufficient. Even if the patient understands what the patient is being asked to do, using existing approaches, it can very difficult for the patient to maintain position and alignment of the patient's eye for any meaningful duration that is required to support the desired quality of images or enable use of lower cost components. For example, OCT is a scanning device that typically requires meaningful time of the patient in front of the device. (more than a few seconds)

Affordable Ophthalmic Imaging Devices

Affordable ophthalmic imaging devices and related methods are described herein that are suitable to be employed in a non-clinical environment (e.g., at a patient's home), thereby serving to reduce the cost associated with increased monitoring of progression of a patient's retinal disease. Referring now to the drawings, in which like reference numerals represent like parts throughout the several views, FIG. 1 illustrates a user 12 engaged with an ophthalmic imaging device 10, in accordance with many embodiments, via a viewer assembly 14 of the imaging device 10. The viewer assembly 14 accommodates alignment, by the user 12, of an eye of the user with an optical axis of the imaging device 10. In many embodiments, the imaging device 10 is configured to be placed on a horizontal surface (e.g., a top surface 16 of a table 18) and rest on the horizontal surface through an imaging time period of the imaging device 10. In many embodiments, the imaging device 10 has an optical axis that extends at an angle from 45 degrees to 85 degrees from the horizontal surface 16 on which the ophthalmic imaging device 10 is supported. In many embodiments, the viewer assembly 14 is configured to interface with regions of the head of the user 12 surrounding the eyes of the user 12 (e.g., the forehead and cheeks of the user) to stabilize the user's head in a suitable position and orientation relative to the optical axis. In many embodiments, the imaging device 10 conducts imaging over a relatively long period of time (e.g., 30 seconds) and the user 12 engages the user's head with the viewer assembly 14 to stabilize the position and orientation of the user's head relative to the optical axis over the imaging period. In many embodiments, the viewer assembly 14 accommodates different positions and/or orientations of the user's head relative to the optical axis so as to enable alignment, by the user, of one of the user's eyes with the optical axis. The combination of the optical axis being angled relative to horizontal and the configuration of the viewer assembly 14 enables the user 12 to self-align an eye of the user with the optical axis of the imaging device 10 and maintain the position of the eye relative to the optical axis over the imaging period while sitting in a natural, comfortable position. The combination of the optical axis being angled relative to horizontal by more than 45 degrees and the configuration of the viewer assembly 14 also effectively inhibits gravity induced downward movement by the user 12 during the applicable imaging period. The combination of the optical axis being angled relative to the horizontal coupled with a suitable height, enables a comfortable position of the user of a desktop device, and results in a stable position with minimal drift due to gravity. In many embodiments, the resulting ophthalmic imaging device is portable and provides a user friendly cost effective solution for at home monitoring of a retinal disease.

In many embodiments, the optical axis of the ophthalmic imaging device is angled between 45 and 85 degrees relative to the horizontal surface. In some embodiments, the angle of the ophthalmic imaging device relative to the horizontal surface can be adjusted by the user so as to achieve a comfortable position while enabling alignment of the optical axis with the user's pupil while the user's head is positioned against the viewer. In many embodiments, the ophthalmic imaging device is configured to be stationary when not being adjusted or moved by the user and the user can make small lateral adjustments of the user's head relative to viewer and/or the housing of the ophthalmic imaging device (e.g., in axes X and Y perpendicular to the optical axis) to align the optical axis with the user's pupil. In many embodiments, the lateral movement of the user's head relative to the viewer and/or the housing is no more than 20 mm and typically in the order of 0.5 mm or less. In some embodiments, the viewer has a flexibility that accommodates lateral movement of the user's head relative to the housing. For example, the viewer can incorporate a flexible material (e.g., a soft foam) in the margins of the viewer such that the user can push the user's head against one part or the viewer relative to another part of the viewer to laterally reposition the user's head relative to the housing and thereby relative to the optical axis. Alternatively, the ophthalmic imaging device can include a mechanism allowing the viewer to slide laterally relative to the optical axis (e.g., on axes X and/or Y perpendicular to the optical axis) such that the user can tilt and/or reposition the user's head relative to the housing to cause the viewer to slide relative to the housing to bring the user's pupil into alignment with the optical axis.

Figure 2:
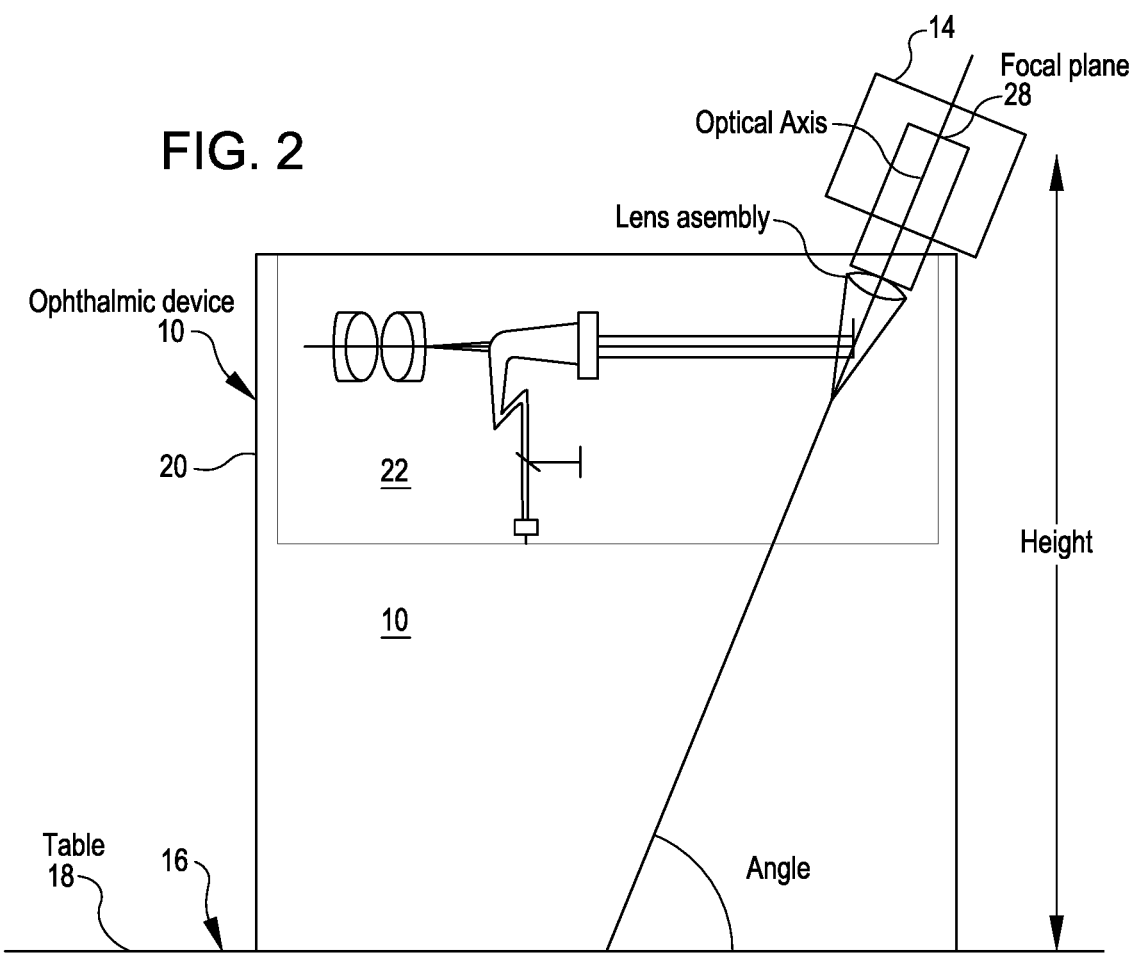
FIG. 2 is a simplified schematic side view illustration of an ophthalmic imaging device configured to be supported on a horizontal surface and orient the optical axis of the imaging device at an angle relative to the horizontal surface, in accordance with many embodiments.

FIG. 2 shows a simplified schematic side view illustration of an embodiment of the ophthalmic imaging device 10. In the illustrated embodiment, the imaging device 10 includes a housing assembly 20 and an imaging assembly 22 mounted to the housing assembly 20, and the viewer assembly 14 mounted to the housing assembly 20. The imaging assembly 22 includes a lens assembly 24. The imaging assembly 22 has an optical axis 26 that is oriented at an angle relative to the top surface 16 of the table 18. In many embodiments, the optical axis 26 extends at an angle from 45 degrees to 85 degrees from the horizontal surface 16 on which the ophthalmic imaging device 10 is supported. In many embodiments, the imaging device 10 has a focal point 28 disposed at a height between 180 mm to 350 mm above the top surface 16.

Figure 3:
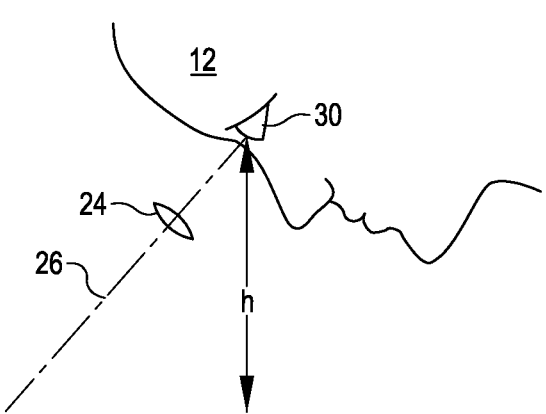
FIG. 3 is a simplified schematic side view illustrating alignment of a user's eye with an optical axis of an ophthalmic imaging device with the optical axis being oriented at an angle relative to horizontal, in accordance with many embodiments.
Figure 4:
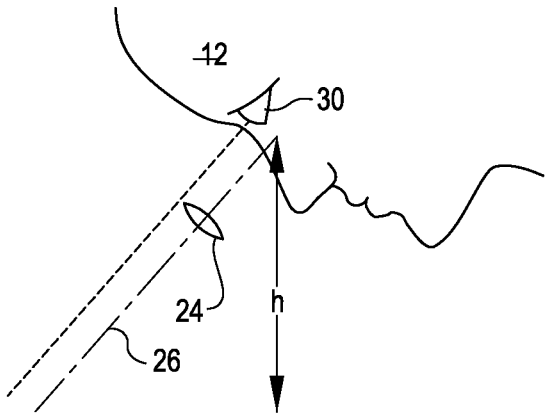
FIG. 4 is a simplified schematic side view illustrating misalignment of a user's eye with an optical axis of an ophthalmic imaging device with the optical axis being oriented at an angle relative to horizontal, in accordance with many embodiments.

In many embodiments, the imaging device 10 is configured to enable the user 12 to achieve alignment of an eye 30 of the user 12 with the optical axis 26 and maintain sufficient alignment of the eye with the optical axis 26 throughout an applicable imaging period of the imaging device 10. For example, when the user 12 is engaged with the viewer assembly 14 such that the user's eye 30 is aligned with the optical axis 26 as illustrated in FIG. 3, continued engagement of the viewer assembly 14 by the user 12 and continued fixation by the user 10 upon a fixation target displayed to the user by the imaging assembly 22 can be used to help maintain alignment of the eye 30 with the optical axis 26 through the applicable imaging period of the imaging device 10. When the user 12 is engaged with the viewer assembly 14 such that the user's eye 30 is misaligned with the optical axis 26 as illustrated in FIG. 4, the user 12 can reposition and/or reorient the user's head relative to the viewer assembly 14 to bring the user's eye 30 into alignment with the optical axis 26. In many embodiments, the imaging device 10 repeatedly images the user's eye 30 and processes the image to determine if the user's eye 30 is aligned with the optical axis 26 or misaligned with the optical axis 26. In many embodiments, if the user's eye 30 is misaligned with the optical axis 26, the imaging device 10 provides feedback to the user 12 regarding what direction and distance the user 12 should reposition the user's eye 30 relative to the optical axis to bring the user's eye 30 into alignment with the optical axis 26.

Figure 5:
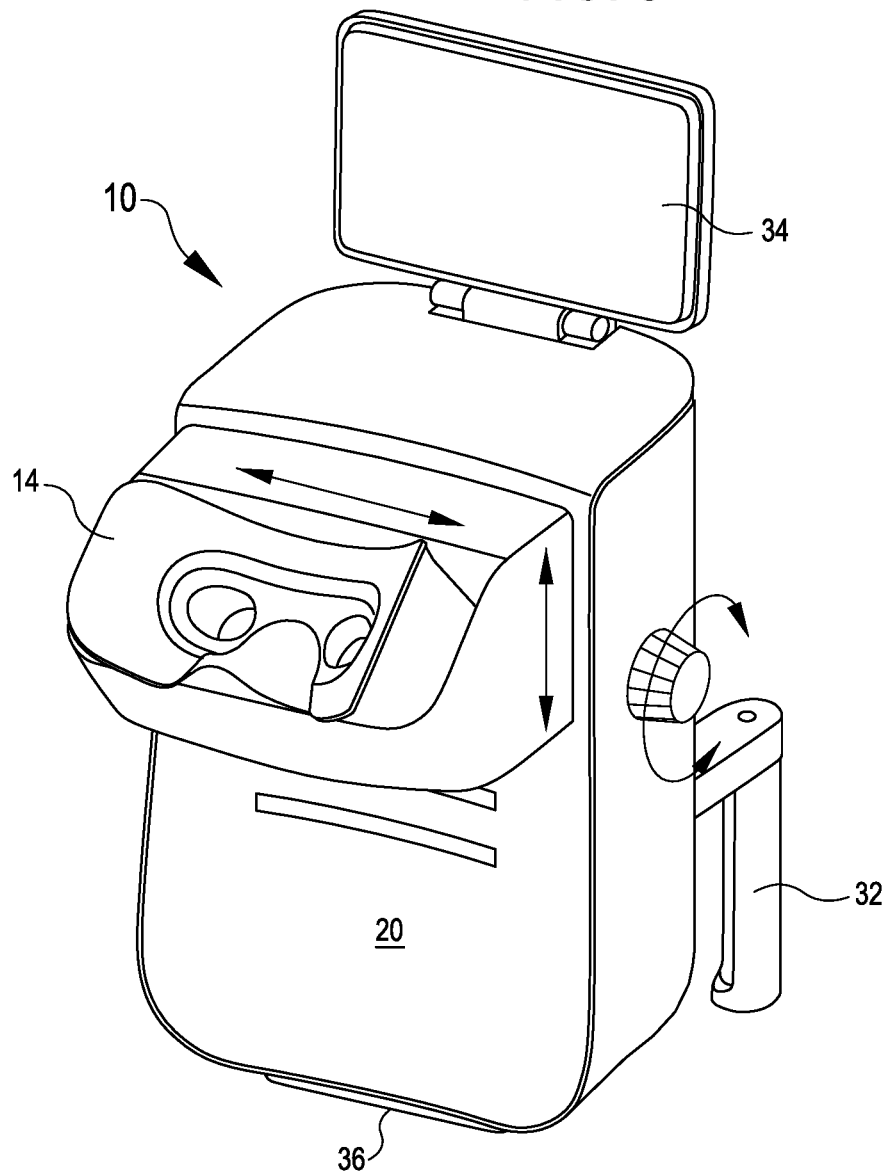
FIG. 5 shows an isometric view image of an ophthalmic imaging device, in accordance with many embodiments.

FIG. 5 shows an embodiment of the ophthalmic imaging device 10. In the illustrated embodiment, the imaging device 10 includes an embodiment of the viewer assembly 14, an embodiment of the housing assembly 20, a pair of handles 32, and a touch-screen user interface 34. The housing assembly 20 includes a height adjustment knob 35 and an adjustable base 36. The height adjustment knob 35 is drivingly coupled with the adjustable base 36, which is adjustable via rotation of the knob 35 to change the elevation of the viewer assembly 14 relative to the horizontal surface 16 used to support the imaging device 10. In the illustrated embodiment, rotating the knob 35 in one direction increases the elevation of the viewer assembly 14 relative to the horizontal surface 16. Rotating the knob 35 in the other direction decreases the elevation of the viewer assembly 14 relative to the horizontal surface 16. The pair of handles 32 are configured to be held by the user 12 to hold the viewer assembly 14 in engagement with the user's head so as to help maintain alignment of the user's eye 30 during the applicable imaging period of the imaging device 10.

Figure 6:
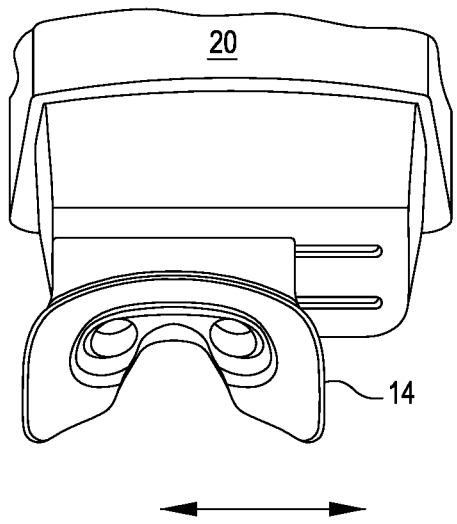
FIG. 6 shows a top view image of the ophthalmic imaging device of FIG. 5 with a viewer assembly of the imaging device positioned for imaging of a user's right eye.
Figure 7:
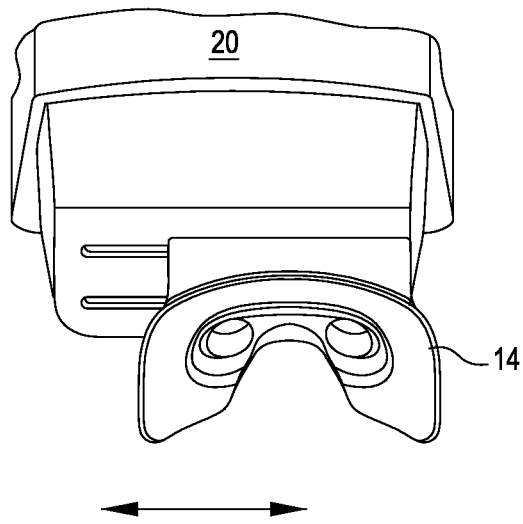
FIG. 7 shows a top view image of the ophthalmic imaging device of FIG. 5 with the viewer assembly positioned for imaging of a user's left eye.

In many embodiments, the viewer assembly 14 is repositionable relative to the housing assembly 20 between a configuration for imaging of the user's right eye and a configuration for imaging of the user's left eye. For example, FIG. 6 shows a top view image of the ophthalmic imaging device 10 with the viewer assembly 14 positioned for imaging of the user's right eye. FIG. 7 shows a top view image of the ophthalmic imaging device 10 with the viewer assembly 14 positioned for imaging of a user's left eye. In some embodiments, the imaging device 10 includes a repositioning mechanism by which the viewer assembly 14 is coupled with the housing assembly 20. For example, in the illustrated embodiment, the viewer assembly 14 is slideably coupled with the housing assembly 20 via a repositioning mechanism that provides for sliding of the viewer assembly 14 relative to the housing assembly 20 between the respective configurations for imaging of each of the user's eyes.

Figure 8:
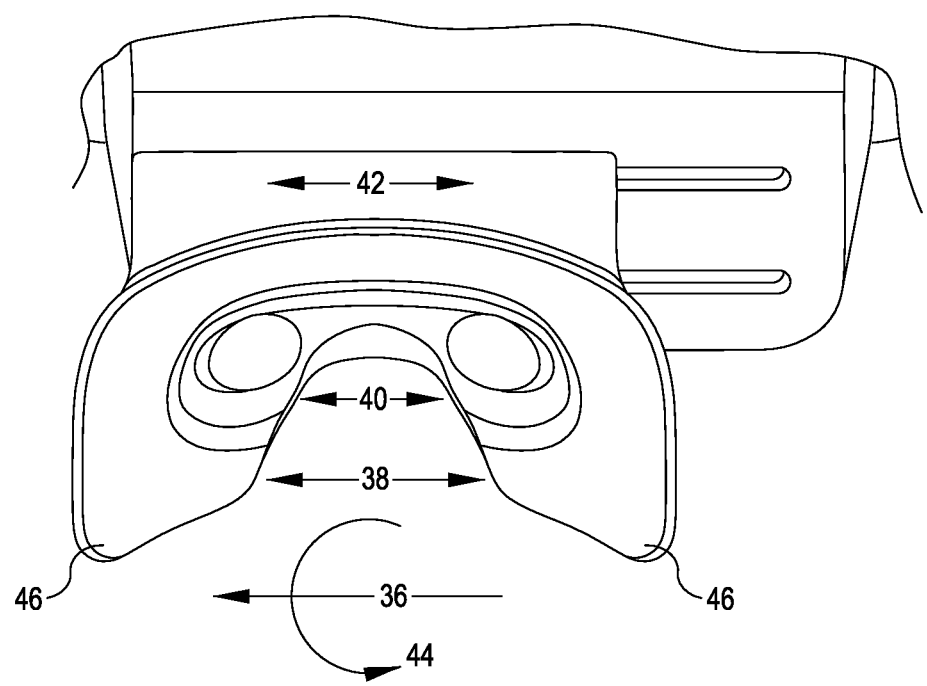
FIG. 8 shows a close-up top view image of the viewer assembly of the ophthalmic imaging device of FIG. 5.

In many embodiments, the viewer assembly 14 is configured to accommodate different positions and/or orientations of the user's head relative to the optical axis 26 so as to enable alignment, by the user 12, of the eye 30 with the optical axis 26. For example, FIG. 8 shows a close-up top view image of the viewer assembly 24 of the ophthalmic imaging device 10. In the illustrated embodiment, the viewer assembly 24 has gaps 38, 40 that accommodate the user's nose for different positions and/or orientations of the user's head relative to the viewer assembly 14. Specifically, the gaps 38, 40 are sized to accommodate different lateral positions (i.e., parallel to axis 42) of the user's head and nose relative to the viewer assembly 14. The gaps 38, 40 are sized to accommodate different orientations (i.e., in directions 44) of the user's head relative to the viewer assembly 14. The depth of the recess in the viewer assembly 14 provided by the gaps 38, 40 is sized to accommodate different tilting orientations (e.g., about axis 36) of the user's head relative to the viewer assembly 14 and different vertical positions (perpendicular to axis 42) of the user's head relative to the viewer assembly 14 to enable the user to adjust the vertical position of the user's eye to enable the user to engage the user's head with the viewer assembly 14 in which the user's eye is aligned with the optical axis 26.

In many embodiments, the viewer assembly 14 has an interface surface 46 that is configured to engage the user's head continuously along a perimeter segment that surrounds the user's eyes. In many embodiments, the perimeter segment extends continuously from below the user's left eye, around the user's left eye between the user's left eye and the user's left ear, above the user's eyes, around the user's right eye between the user's right eye and the user's right ear, to below the user's right eye. In many embodiments, the interface surface 46 is configured to accommodate the different positions and/or orientations of the user's head relative to the optical axis 26. In many embodiments, the viewer assembly 14 is deformable so that the shape of interface surface 46 is conformable to the user's head to accommodate the different positions and/or orientations of the user's head relative to the optical axis. In many embodiments, the viewer assembly includes a base component, a deformable component mounted to the base component, and a biocompatible layer that covers the deformable component. In many embodiments, the biocompatible layer includes the interface surface 46. In some embodiments, the deformable component has different degrees of deformability in different regions of the interface surface.

Figure 9:
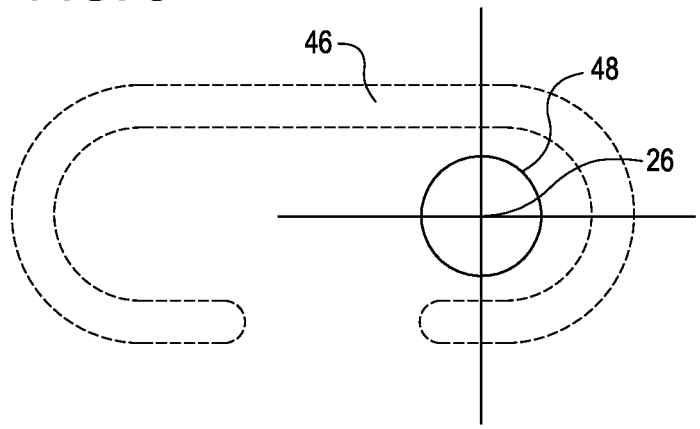
FIG. 9 is a simplified schematic illustration of the position and orientation of an interface surface of a viewer assembly of an ophthalmic imaging device relative to the optical axis of the ophthalmic imaging device, in accordance with many embodiments.
Figure 10:
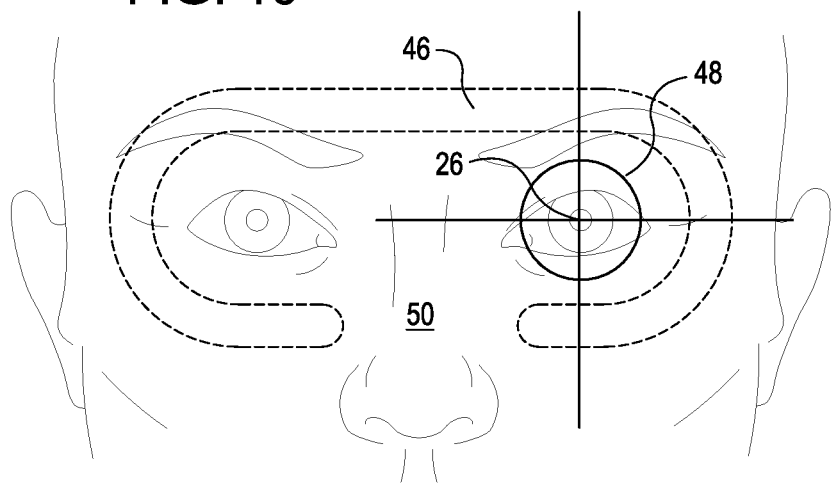
FIG. 10 is a simplified schematic illustration of the position and orientation of the interface surface of the viewer assembly of FIG. 9 and a first user with the left eye of the first user aligned with the optical axis of the ophthalmic imaging device.
Figure 11:
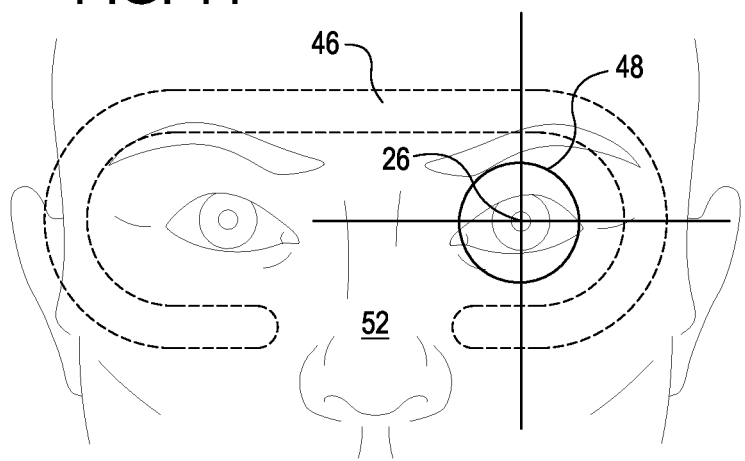
FIG. 11 is a simplified schematic illustration of the position and orientation of the interface surface of the viewer assembly of FIG. 9 and a second user with the left eye of the second user aligned with the optical axis of the ophthalmic imaging device.

In many embodiments, the viewer assembly 14 accommodates different positions and/or orientations of each of a plurality of different user's heads relative to the optical axis 26 so as to enable alignment, by the respective user, of one of the respective user's eye with the optical axis 26. For example, the plurality of different user's accommodated by the viewer assembly 14 can have a plurality of different distances by which the eyes of the respective user are separated. FIG. 9 is a simplified schematic illustration of the position and orientation of the interface surface 46 of the viewer assembly 14 relative to the optical axis 26 and an aperture 48 of the imaging device 10 through which the imaging assembly 22 images the eye 30. FIG. 10 is a simplified schematic illustration of the position and orientation of the interface surface 46, the optical axis 26, and the aperture 48 relative to a first user 50 with the left eye of the first user 50 aligned with the optical axis 26. FIG. 11 is a simplified schematic illustration of the position and orientation of the interface surface 46, the optical axis 26, and the aperture 48 relative to a second user 52 with the left eye of the second user 52 aligned with the optical axis 26. As illustrated in FIG. 10 and FIG. 11, the eyes of the first user 50 are separated by a greater distance as compared to the eyes of the second user 52 and the viewer assembly 14 accommodates use of the imaging device 10 by both the first user 50 and the second user 52.

FIG. 12 shows an ophthalmic imaging device 110 that is configured the same as the ophthalmic imaging device 10, except for some notable differences described herein. The imaging device 110 includes a housing assembly 120 and a base assembly 130 instead of the housing assembly 20 and the adjustable base 36 of the imaging device 10. The housing assembly 120 is slideably mounted to the base assembly 130. The housing assembly 120 includes a lift knob 122 that is drivingly coupled with a positioning mechanism configured to selectively translate the housing assembly 120 relative to the base assembly 130. The position of the housing assembly 120 relative to the base assembly 120 is selectively adjustable via selective rotation of the lift knob 122. The base assembly 130 includes an L-shaped base member 132 configured to rest on a flat surface and provide stable support for the imaging device 110. The base assembly 130 includes the pair of handles 32, which are mounted to the base member 132. The pair of handles 32 are configured to be held by the user 12 to hold the viewer assembly 14 in engagement with the user's head so as to help maintain alignment of the user's eye 30 during the applicable imaging period of the imaging device 110. In the imaging device 110, the viewer assembly 14 is mounted to the housing assembly 120, and repositionable relative to the housing assembly 120, the same as described herein with respect to the viewer assembly 14 and the housing assembly 20 of the ophthalmic imaging device 10, and as illustrated in FIG. 6, FIG. 7, and FIG. 8. The touch-screen user interface 34 is fixedly mounted to an upper portion of the housing assembly 120 instead of being pivotally mounted to the housing assembly 20 as in the imaging device 10. The imaging device 110 includes a volume control knob 140 operable to adjust volume level of audible indications and/or instructions output by the imaging device 110, such as audible instructions to the user 12 during an imaging session.

Many embodiments of the imaging devices 10, 110 include a locking mechanism configured to inhibit (and in some embodiments prevent) inadvertent movement of the viewer assembly 14 relative to the housing assembly 20, 120 during an imaging session. Any suitable locking mechanism can be employed. For example, FIG. 13, FIG. 14, and FIG. 15 illustrate a locking mechanism 200 that inhibits sliding of the viewer assembly 14 relative to the housing assembly 20, 120 while the viewer assembly 14 is engaged by the user's 12 head. In the illustrated embodiment, the locking mechanism 200 includes a right roller 202 and a left roller 204. The right roller 202 is mounted to the viewer assembly 14 for rotation around a right pivot axis 206. The left roller 204 is mounted to the viewer assembly 14 for rotation around a left pivot axis 208. The outer circumferential rolling surface of each of the right roller 202 and the left roller 204 interfaces with the housing assembly 20, 120. The housing assembly 20, 120 includes a detent feature 210 that includes a left ramp 212, a left detent groove 214, a right ramp 216, and a right detent groove 218. As described herein, the viewer assembly 14 is slideably repositionable relative to the housing assembly 20, 120 between a right eye imaging position for imaging of the user's right eye and a left eye imaging position for imaging of the user's left eye. When the viewer assembly 14 is in the right eye imaging position (as illustrated in FIG. 15), the right roller 202 is disposed in the right detent groove 218. When the user 12 rests the user's head on the viewer assembly 14, the force applied to the viewer assembly 14 by the user's head pushes the right roller 202 into the right detent groove 218, which increases the amount of lateral force that would have to be applied to the viewer assembly 14 to displace the right roller 202 from the right detent groove 218, thereby inhibiting or preventing lateral movement of the viewer assembly 14 relative to the housing assembly 20, 120 while the user's head is rested on the viewer assembly 14. In some embodiments, each of the right roller 202 and the left roller 204 include a respective O-ring that is made from a resilient material and deforms in response to the force applied to the viewer assembly 14 by the user's head so as to further inhibit displacement of the roller 202, 204 from the respective detent groove 218, 214. When the user's head is not resting on the viewer assembly 14, the right roller 202, the left roller 204, and the detent feature 210 are configured to accommodate repositioning of the viewer assembly 14 between the right eye imaging position and the left eye imaging position. For example, when the viewer assembly 14 is moved in direction 220 (relative to the housing assembly 20, 120) to reposition the viewer assembly 14 from the right eye imaging position to the left eye imaging position, the right roller 202 rolls out of the right detent groove 218 and then down the right ramp 216, and the left roller 204 then rolls up the left ramp 212 and into the left detent groove 214. Likewise, when the viewer assembly 14 is moved in direction 222 (relative to the housing assembly 20, 120) to reposition the viewer assembly 14 from the left eye imaging position to the right eye imaging position, the left roller 204 rolls out of the left detent groove 214 and then down the left ramp 212, and the right roller 202 then rolls up the right ramp 216 and into the right detent groove 218.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

Examples of the embodiments of the present disclosure can be described in view of the following clauses:

Clause 1. An ophthalmic imaging device, comprising: an imaging assembly having an optical axis; a housing assembly to which the imaging assembly is attached, wherein the housing assembly is configured to rest on a horizontal surface during operation of the imaging assembly, and wherein the optical axis is oriented at an angle from 45 degrees to 85 degrees from the horizontal surface when the housing assembly rests on the horizontal surface; and a viewer assembly coupled with the housing assembly, the viewer assembly comprising an interface surface shaped to engage a user's head to stabilize a position and an orientation of the user's head relative to the optical axis, the viewer assembly accommodating different positions and/or orientations of the user's head relative to the optical axis so as to enable alignment, by the user, of one of the user's eyes with the optical axis.

Clause 2. The ophthalmic imaging device of clause 1, wherein: the interface surface is configured to engage the user's head continuously along a perimeter segment that surrounds the user's eyes; and the perimeter segment extends continuously from below the user's left eye, around the user's left eye between the user's left eye and the user's left ear, above the user's eyes, around the user's right eye between the user's right eye and the user's right ear, to below the user's right eye.

Clause 3. The ophthalmic imaging device of any preceding clause, wherein the interface surface is configured to accommodate the different positions and/or orientations of the user's head relative to the optical axis.

Clause 4. The ophthalmic imaging device of any preceding clause, comprising an aperture through which the imaging assembly images the one of the user's eyes aligned with the optical axis, and wherein viewer assembly comprises a light blocking side surface that extends between the interface surface and the aperture to block light continuously along the interface surface.

Clause 5. The ophthalmic imaging device of any preceding clause, wherein the viewer assembly is deformable so that the shape of interface surface is conformable to the user's head to accommodate the different positions and/or orientations of the user's head relative to the optical axis.

Clause 6. The ophthalmic imaging device of clause 5, wherein: the viewer assembly comprises a base component, a deformable component mounted to the base component, and a biocompatible layer that covers the deformable component; and the biocompatible layer includes the interface surface.

Clause 7. The ophthalmic imaging device of any preceding clause, wherein: the viewer assembly accommodates different positions and/or orientations of each of a plurality of different user's heads relative to the optical axis so as to enable alignment, by the respective user, of one of the respective user's eye with the optical axis; and the plurality of different users comprise a plurality of different distances by which the eyes of the respective user are separated.

Clause 8. The ophthalmic imaging device of any preceding clause, wherein the interface surface is configured to engage the user's forehead.

Clause 9. The ophthalmic imaging device of any preceding clause, wherein the interface surface is configured to engage each of the user's cheeks.

Clause 10. The ophthalmic imaging device of any preceding clause, wherein: the imaging assembly has a focal point; and the focal point is disposed at a height between 180 mm to 350 mm above the horizontal surface when the housing assembly rests on the horizontal surface.

Clause 11. The ophthalmic imaging device of clause 10, wherein the housing assembly is adjustable to change the height at which the focal point is disposed above the horizontal surface.

Clause 12. The ophthalmic imaging device of clause 11, wherein the housing assembly comprises a pair of legs that can be adjusted to change the height at which the focal point is disposed above the horizontal surface.

Clause 13. The ophthalmic imaging device of any of clause 10 through clause 12, wherein: the housing assembly is adjustable to simultaneously change the height at which the focal point is disposed above the horizontal surface and the orientation of the optical axis relative to the horizontal surface; and each respective height has a corresponding unique angle of the optical axis relative to the horizontal surface.

Clause 14. The ophthalmic imaging device of any preceding clause, wherein the different positions and/or orientations of the user's head accommodated by the viewer assembly enable repositioning of the user's eye by 20 mm along any axis perpendicular to the optical axis.

Clause 15. The ophthalmic imaging device of any preceding clause, wherein the housing assembly includes a pair of handles configured to be held by the user to hold the viewer assembly in engagement with the user's head.

Clause 16. The ophthalmic imaging device of any preceding clause, further comprising a repositioning mechanism by which the viewer assembly is coupled to the housing assembly, the repositioning mechanism configured to enable repositioning of the viewer assembly relative to the housing assembly to enable separate alignment of each of the user's eyes with the optical axis.

Clause 17. The ophthalmic imaging device of clause 16, wherein the viewer assembly is slideably coupled with the housing assembly via the repositioning mechanism.

Clause 18. The ophthalmic imaging device of clause 17, wherein the viewer assembly is slideably relative to the housing assembly via the repositioning mechanism in two different directions transverse to the optical axis.

Clause 19. The ophthalmic imaging device of any of clause 16 through clause 18, wherein the repositioning mechanism is operable to reposition the viewer assembly relative to the focal point parallel to the optical axis.

Clause 20. The ophthalmic imaging device of any preceding clause, wherein the housing assembly is adjustable to change the angle at which the optical axis is oriented relative to the horizontal surface.

Clause 21. The ophthalmic imaging device of clause 20, wherein the housing assembly comprises a pair of legs that can be adjusted to change the angle at which the optical axis is oriented relative to the horizontal surface.

What is claimed is:

1. An ophthalmic imaging device, comprising:
    a retinal imaging assembly having an optical axis;
    a housing assembly to which the retinal imaging assembly is attached, wherein the housing assembly is configured to rest on a horizontal surface during operation of the retinal imaging assembly, wherein the optical axis is oriented at an angle from the horizontal surface when the housing assembly rests on the horizontal surface, and wherein the angle is in a range from 45 degrees to 85 degrees from the horizontal surface; and
    a viewer assembly coupled with the housing assembly, the viewer assembly comprising an interface surface shaped for engagement with each head of a plurality of different user's and to accommodate repositioning of the head to align a pupil of the user with the optical axis;
    wherein the ophthalmic imaging device has a first configuration for use during respective imaging sessions of a first eye of each of the different users by the retinal imaging assembly;
    wherein the optical axis, in the first configuration of the retinal imaging assembly, has a fixed position and orientation relative to the viewer assembly; and
    wherein the interface surface, in the first configuration of the retinal imaging assembly, accommodates repositioning, during each of the respective imaging sessions and by the respective user, of the respective user's head relative to the interface surface to reposition the first eye of the user in a direction transverse to the optical axis onto the optical axis.

2. The ophthalmic imaging device of claim 1, wherein the retinal imaging assembly comprises an optical coherence tomography imaging assembly.

3. The ophthalmic imaging device of claim 1, wherein the interface surface is configured to accommodate different positions and/or orientations of each of the different user's heads relative to the viewer assembly while the retinal imaging assembly is in the first configuration and during each of the respective imaging sessions.

4. The ophthalmic imaging device of claim 1, wherein the interface surface, in the first configuration of the ophthalmic imaging device, accommodates repositioning during each of the respective imaging sessions of the respective user's eye by 20 mm relative to the viewer assembly in any direction perpendicular to the optical axis.

5. The ophthalmic imaging device of claim 1, wherein:
    the viewer assembly comprises a recess configured to accommodate a nose of the user when the user's head is engaged with the interface surface; and
    the recess is configured to accommodate different positions of the nose within the recess to accommodate repositioning, during the imaging session, of the eye by the user transverse to the optical axis in a vertical direction and a horizontal direction to reposition the eye onto the optical axis while the ophthalmic imaging device is in the first configuration.

6. The ophthalmic imaging device of claim 1, comprising an aperture through which the retinal imaging assembly images the first eye of the user positioned on the optical axis, and wherein viewer assembly comprises a light blocking side surface that extends between the interface surface and the aperture to block light continuously along the interface surface.

7. The ophthalmic imaging device of claim 1, wherein:
the interface surface is configured to engage each of the different user's heads continuously along a perimeter segment that surrounds the user's eyes; and
the perimeter segment extends continuously from below the user's left eye, around the user's left eye between the user's left eye and the user's left ear, above the user's eyes, around the user's right eye between the user's right eye and the user's right ear, to below the user's right eye.

8. The ophthalmic imaging device of claim 1, wherein the viewer assembly is deformable so that the interface surface is conformable to each of the different user's heads to accommodate different positions and/or orientations of the user's head relative to the viewer assembly.

9. The ophthalmic imaging device of claim 8, wherein:
the viewer assembly comprises a base component, a deformable component mounted to the base component, and a biocompatible layer that covers the deformable component; and
the biocompatible layer includes the interface surface.

10. The ophthalmic imaging device of claim 1, wherein the viewer assembly is configured to accommodate a plurality of different distances by which the eyes of the respective user are separated.

11. The ophthalmic imaging device of claim 1, wherein the interface surface is configured to engage the user's forehead and each of the user's cheeks for each of the different users.

12. The ophthalmic imaging device of claim 1, wherein:
the retinal imaging assembly has a focal point; and
the housing assembly comprises a pair of legs that can be adjusted to change a height at which the viewer assembly is disposed above the horizontal surface.

13. The ophthalmic imaging device of claim 1, wherein the housing assembly includes a pair of handles configured to be held by each of the respective users to hold the viewer assembly in engagement with the user's head.

14. The ophthalmic imaging device of claim 1, further comprising a repositioning mechanism by which the viewer assembly is coupled to the housing assembly, the repositioning mechanism configured to enable repositioning of the viewer assembly relative to the housing assembly to a second configuration of the ophthalmic imaging device for use during imaging sessions of a second eye of each of the different users by the retinal imaging assembly, wherein the second configuration accommodates repositioning during imaging sessions of the second eye of the user and by the user, relative to the viewer assembly so as to reposition the second eye transverse to the optical axis to reposition the second eye onto the optical axis, and wherein the optical axis, in the second configuration of the ophthalmic imaging device, has a fixed position and orientation relative to the viewer assembly.

15. The ophthalmic imaging device of claim 14, wherein the viewer assembly is slideably coupled with the housing assembly via the repositioning mechanism.

16. The ophthalmic imaging device of claim 15, further comprising a locking mechanism configured to inhibit sliding of the viewer assembly relative to the housing assembly while the viewer assembly is engaged by the user's head.

17. The ophthalmic imaging device of claim 1, wherein the retinal imaging assembly is configured to image the eye of the user to determine if the eye of the user is offset transverse to the optical axis and provide feedback to the user indicating what direction the user should reposition the eye, relative to the viewer assembly, transverse to the optical axis to reposition the eye onto the optical axis.

* * * * *